(12) United States Patent
Pande et al.

(10) Patent No.: US 6,207,161 B1
(45) Date of Patent: Mar. 27, 2001

(54) INDUCTION OF CYTOLYTIC T-LYMPHOCYTES WITH CYTOMEGALOVIRUS POLYPEPTIDES

(75) Inventors: Hema Pande; John A. Zaia, both of Arcadia, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 08/256,104

(22) PCT Filed: Jun. 25, 1992

(86) PCT No.: PCT/US92/05432

§ 371 Date: Aug. 31, 1994

§ 102(e) Date: Aug. 31, 1994

(87) PCT Pub. No.: WO94/00150

PCT Pub. Date: Jan. 6, 1994

Related U.S. Application Data (60) Continuation-in-part of application No. 07/307,526, filed on Feb. 8, 1989, now abandoned, which is a division of application No. 06/885,386, filed on Jul. 16, 1986, now abandoned, which is a continuation of application No. 06/635,368, filed on Jul. 27, 1994, now abandoned.

(51) Int. Cl.[7] .......................... A61K 39/245; C12N 7/00; C12N 14/045; C12N 5/22

(52) U.S. Cl. ..................................... 424/186.1; 424/230.1; 530/324; 530/326; 530/327; 530/328; 435/325; 435/372.3; 435/377

(58) Field of Search .................. 435/372.3, 325, 435/377; 424/186.1, 230.1; 530/328, 324, 403, 326, 327; 514/12–16

(56) References Cited

FOREIGN PATENT DOCUMENTS 88 07077    9/1988   (WO) .

OTHER PUBLICATIONS

Borysiewicz et al, Eur. J. Immunol. 13:804–809, 1983.*
H. Pande et al., *Virology*, vol. 182 (1991), pp. 220–228.
H. Pande et al., *Virology*, vol. 178 (1990), pp. 6–14.
M. Ohlin et al., *Clin. Exp. Immunol.*, vol. 84 (1991), pp. 508–514.
B. Ruger et al., *Journal of Virology*, vol. 61, No. 2 (1987), pp. 446–453.
P. Greenberg et al., *Annals New York Academy of Sciences*, vol. 636 (1991), pp. 184–195.
European Search Report dated Feb. 29, 1996 for related patent application EP 92915562.0.

* cited by examiner

*Primary Examiner*—Mary E. Mosher
(74) *Attorney, Agent, or Firm*—Rothwell, Figg, Ernst & Manbeck (57) ABSTRACT

Immunogens for use in human cytomegalovirus vaccines or skin tests which comprise human cytomegalovirus matrix proteins or fractions thereof are disclosed. It is also disclosed that such matrix proteins are target antigens for human cytomegalovirus specific cytotoxic T-lymphocytes.

15 Claims, 4 Drawing Sheets

INDUCTION OF CYTOLYTIC T-LYMPHOCYTES WITH CYTOMEGALOVIRUS POLYPEPTIDES

RELATED APPLICATION

This application is a U.S. National application under 35 U.S.C. 371 of PCT/US92/05432, filed Jun. 25, 1992, which is a continuation-in-part of application Ser. No. 07/307,526 filed Feb. 8, 1989, abandoned, which is a division of application Ser. No. 06/885,386 filed Jul. 16, 1986, abandoned, which is a continuation of application Ser. No. 06/635,368 filed Jul. 27, 1984 and now abandoned.

This invention was made with government support under Grants No. PO1 CA30206 and P30 CA33572 awarded by the National Cancer Institute and by the National Institutes of Health. The government has certain rights in the invention.

FIELD OF THE INVENTION

This invention relates to human cytomegalovirus (HCMV) vaccines in which the immunogen is an HCMV matrix protein or a fragment of such a protein. This invention also relates to immunologic cytomegalovirus proteins or peptides that induce cytolytic T-lymphocytes effective to lyse cytomegalovirus infected cells, to the production of such proteins or peptides and to vaccines and skin tests in which such proteins or peptides are utilized.

ABBREVIATIONS

| | |
|---|---|
| CMV | Cytomegalovirus |
| HCMV | Human Cytomegalovirus |
| CTL | Cytotoxic T-lymphocytes |
| MHC | Major Histocompatibility Complex |
| IE | Immediate Early |
| gB | Glycoprotein B |
| CNBr | Cyanogen Bromide |
| HF | Human Foreskin Fibroblasts |
| FCS | Fetal Calf Serum |
| PBL | Peripheral Blood Lymphocytes |
| APC | Antigen Presenting Cell |
| ActD | Actinomycin D |
| pp65 | An HCMV Matrix Protein--corresponds to "gp64" of Ser. No. 07/307,526 |
| TFA | Trifluoroacetic acid |

REFERENCES

1. Sissons, J. G. P., et al., *Immunol Today* 7:57 (1986).
2. Alford, C. A., et al., *Virology*, 2nd ed., B. N. Fields, D. M. Knipe, et al. Eds., Raven Press, New York (1990).
3. Ho, M. *Cytomegalovirus: Biology and Infection*, 2nd edition, pp. 249–300, Plenum Medical Book Co., New York (1991).
4. Rand, K. H., et al., *N.Engl.J.Med.* 298:951 (1978).
5. Neiman, P., et al., *Transplantation* 15:478 (1973).
6. Quinnan, G. V., et al., *N.Engl.J. Med.* 307:7 (1982).
7. Quinnan, G. V., et al. *Rev. Infect. Dis.* 6:156 (1984).
8. Borysiewicz, L. K., et al., *Eur. J. Immunol.* 18:269 (1988).
9. Reusser, P., et al., *Blood* 78:1373 (1991).
10. Borysiewicz, L. K., et al., *J. Exp. Med.* 168:919 (1988).
11. Riddell, S. R., et al., *J.Immunol.* 146:2795 (1991).
12. Gooding, L. R., et al., *J.Immunol.* 131:2580 (1983).
13. Townsend, A. R. M., et al., *Cell* 42:457 (1985).
14. Nuchtern, J. G., et al., *Nature* 339:223 (1989).
15. Moore, M. W., et al., *Cell* 54:777 (1988).
16. Townsend, A. R. M., et al., *Cell* 44:959 (1986).
17. Maryanski, J. L., et al., *Nature* 324:578 (1986).
18. Reddehase, M. J., et al., *Nature* 337:651 (1989).
19. Carbone, F. R., et al., *J. Exp. Med.* 167:1767 (1988).
20. Wabuke-Bunoti, M., *J. Immunol.* 127:1122 (1981).
21. Clark, B. R., et al., *J. Virol.* 49:279 (1984).
22. Riddell, S. R., et al., *J.Immunol. Methods* 128:189 (1990).
23. Pande, H., et al., *Virology*, 178:6–14 (1990).
24. Borysiewicz, L. K., et al., *Eur.J.Immunol.* 13:804 (1983).
25. Stinski, M. F., *J.Virol.* 26:686 (1978).
26. Wathen, M. W., et al., *J.Virol.* 41:462 (1982).
27. Geballe, A., et al., *J.Virol.* 57:864 (1986).
28. Reddehase, M. J., et al., *J.Virol.* 55:264 (1985).
29. Koszinowski, U. H., et al., *Current Top.Microbiol. Immunol.* 154:189 (1990).
30. Reddehause, M. J., et al., *Nature* 312:369 (1984).
31. Reddehause, M. J., et al., *J.Virol.* 61:3102 (1987).
32. Berzofsky, J. A., *J.Clin.Invest.* 82:1811 (1988).
33. Townsend, A., et al., *Nature* 340:433 (1989).
34. Braciale, T. J., et al., *Immunol.Rev.* 98:95 (1987).
35. Forman, S. J., et al., *J.Immunol.* 134:3391 (1985).
36. Deres, K., et al., *Nature* 342:561 (1989).
37. Watari, E., et al., *J.Exp.Med.* 165:459 (1987).
38. Greenberg, P. D., et al., *Ann.N.Y.Acad.Sci.*, In press.
39. Plotkins, et al., *Infection and Immunity* 12:521–527 (1975).

BACKGROUND OF THE INVENTION

Cytomegalovirus (CMV) infection is a frequent pathogen in humans. It is usually associated with asymptomatic primary infection, followed by a state of viral persistence or latency (1, 2). In patients with congenital or acquired immune deficiencies and those undergoing solid organ or bone marrow transplantation, primary CMV infection and reactivation of persistent CMV have frequently been associated with life-threatening invasive visceral disease (3, 5).

Application Ser. No. 07/307,526 reports T-lymphocyte reactivity to the matrix protein of HCMV following natural infection of an individual. As that application explains, peripheral blood mononuclear leukocytes were separated using Ficoll-hypaque, washed, suspended in RPMI-1640 medium with ten percent (10%) AB+, Rh+ human serum and were then cultured at 37° C. in microtiter plates ($10^5$ cells/well). Different samples of the peripheral blood mononuclear leukocytes were then stimulated with optimal dilutions of either (a) the matrix protein of human cytomegalovirus (HCMVgp64) such as HCMVgp64, (b) HCMV-infected cell lysate or (c) control cell lysate, and cultures were analyzed for cell proliferation and for lymphokine production.

The matrix protein of human cytomegalovirus (4 μg/ml) stimulated $H^3$-thymidine in HCMV seropositive donor peripheral blood mononuclear leukocytes but not in seronegative donor peripheral blood mononuclear leukocytes. The peripheral blood mononuclear leukocytes produced the same stimulation with HCMV-infected cell lysate as when the matrix protein of human cytomegalovirus (HCMVgp64) was used. The matrix protein of human cytomegalovirus (HCMVgp64) induced interleukin-2 (IL-2) production, IL-2 receptor expression and interferon production. The addition of antibody to the IL-2 receptor blocked the reactivity of the peripheral blood mononuclear leukocytes to HCMVgp64.

The development of cell-mediated immunity, particularly that involving CD8+ class I MHC-restricted CMV-specific CTL, represents an essential host factor in the control of persistent infection and the recovery from CMV disease (6, 9). The importance of CD8+ CTL responses in providing protective immunity in CMV seropositive individuals has fostered studies to elucidate the specificity of this response for selected CMV antigens with the objective of developing methods to augment CTL responses in immunocompromised hosts. Studies using vaccinia recombinant viruses to express the non-structural 72 KD CMV immediate early protein (IE) and the major envelope glycoprotein, gB, have demonstrated that in two CMV seropositive individuals, a subset of CTL recognized IE and a minor subset recognized gB (10). However, the majority of CMV-specific CTL in these individuals recognized other undefined viral antigens (10).

It is now established that CD8+ CTL recognize peptide fragments of antigens, derived as a result of intracellular processing of cytoplasmic protein and subsequent association with class I MHC molecules in the endoplasmic reticulum prior to cell surface presentation (12, 13, 14, 15). Consequently, small protein fragments or synthetic viral peptides can sensitize uninfected target cells by direct association with MHC molecules at the cell surface (16, 17, 18). Thus, an alternative approach to using recombinant expression vectors for examining the specificity of CTL recognition is to directly sensitize target cells by incubation with synthetic peptides or peptides derived from native protein by proteolytic digestion (19, 20).

SUMMARY OF THE INVENTION

This invention includes the discovery that HCMV matrix protein pp65 is a target antigen for HCMV specific CTL. CNBr cleavage of pp65 yields other CTL specific target antigens. Immunogens for use in HCMV vaccines or skin tests are provided by pp65 and by identification and synthesis of cytolytic pp65 sequences, e.g., the sequences 1 to 6 (Sequence ID Nos. 1–6), infra. An important advantage of this aspect of the invention is the simplicity and rapidity with which it can be determined whether an individual viral protein functions as a CTL target antigen without the construction of recombinant vectors. The need to synthesize substantial amounts of a large protein is avoided.

EXPERIMENTAL

Virus and Cell Lines

CMV Towne strain was grown in human foreskin fibroblast (HF) monolayer cultures and harvested for virus antigen production 120 hours post infection as described by Clark, et al. (21). AD 169 strain CMV was obtained from ATCC and propagated by three serial passages onto confluent 150 cm$^2$ flasks of HF in DMEM supplemented with 2% FCS. Viral stocks were prepared from infectious supernatants when HF cells showed 100% cytopathic effect.

Primary dermal fibroblast lines were established by explant culture of a skin biopsy obtained using a standard procedure from 5 CMV seropositive individuals with the following HLA types: MW—A1, A24, B7, B8; CM—A1, A2, B35, B57; TM—A3, A24, B8, B51; MR—A24, A25, B18, B35; DH—A1, A31, B38, B44. These cells were maintained in DMEM or Waymouths media supplemented with 10–15% FCS (Hyclone Logan, Utah), 2 mM L-glutamine, and penicillin/streptomycin. Fibroblasts were used as target cells after 4–12 passages. Bone marrow derived fibroblasts were obtained from a CMV seropositive transplant donor (SA) of HLA type A28, A30, B18, B35, and maintained in culture for 6 passages prior to use. EBV transformed B lymphoblastoid cell lines (LCL) were generated and maintained as previously described (22).

CMV pp65 Purification and CNBr Cleavage

CMV pp65 was purified from extracellular virion plus dense bodies of CMV by reverse phase high performance liquid chromatography as previously described (23). Purity was assessed by amino acid analysis. For chemical cleavage purified pp65 was dissolved in 60% formic acid and treated with a 100 fold molar excess of CNBr (over methionine residues) overnight. The solvent was evaporated at room temperature overnight under a stream of argon, the residue resuspended in water and lyophilized.

Generation of Cytotoxic Effector Cells

CMV-specific polyclonal CTL were generated from the PBL of CMV seropositive, asymptomatic donors (CM, MR, TM, MW, and DH) using described methods (11, 22, 8). Briefly, PBL were isolated by Histopaque (Sigma, St. Louis, Mo.) gradient centrifugation and suspended in RPMI medium supplemented with 12% human CMV seronegative AB serum, 4 mM L-glutamine, 25 μM 2 mercaptoethanol (Sigma), penicillin and streptomycin (referred to as culture media). 1×10$^7$ PBL were cultured with 5×10$^5$ autologous fibroblasts infected two hours previously with AD169 or Towne strain of CMV at an MOI of 5 in individual wells of a 6 well plate or in 25 cm$^2$ flasks in a final volume of 6 ml culture media. After 7 days, the cultures were restimulated with both autologous CMV-infected fibroblasts, γ-irradiated (3000 rads) autologous PBL, and then supplemented with recombinant IL2 (2–5 U/ml) 2 and 4 days after restimulation. After a total of 14 days in culture the effector cells were harvested and used in a standard Cr$^{51}$ release assay.

To generate pp65-specific CTL, 5×10$^5$ autologous fibroblasts were cultured for 1 hour with 100 μg/ml peptides from CNBr digested pp65 (CNBr pp65) in 0.2 ml DMEM and used to stimulate 1×10⁷ PBL. These cultures were restimulated at 7 days with CNBr pp65 pulsed fibroblasts, and supplemented with IL2 (2–5 U/ml), 2 and 4 days following restimulation. After a total of 14 days in culture, the effector cells were harvested and used in a $Cr^{51}$ release assay. For a single donor, PBL were cultured in the presence of 75 μg/ml CNBr pp65 for 5 days and then assayed for CTL activity.

CD8+ pp65-specific CTL clones were generated from 14 day CTL lines by first depleting CD4+ T cells with OKT4 mAb (Ortho, Raritan, N.J.) and rabbit complement (Pel freeze, Brown Deer, Wis.) and then plating the enriched CD8+ T cells in 96 well round bottom plates at 0.5 cells/well with autologous irradiated (5000 rads) LCL (2×10⁴ cells/well) as feeder cells, and autologous CNBr pp65 pulsed fibroblasts (2×10³ cells/well) as stimulators in 0.2 ml culture media with 50 U/ml of IL2. Wells positive for growth at 14 days were transferred to larger wells and the clones restimulated every 7 days with autologous CNBr pp65 pulsed fibroblasts or CMV-infected fibroblasts, supplemented with irradiated feeder cells and fed with IL2 (60 U/ml) 2 and 4 days following each restimulation.

Chromium Release Assay

A 4 hour chromium release assay was used to assay T cell lines and clones for cytolytic activity. Effector cells were harvested 5 to 7 days after restimulation, washed once in cold PBS and resuspended in RPMI with 10% FCS. Autologous and MHC-mismatched fibroblast target cells were infected with CMV at an MOI=5 for 24 hours or incubated in the presence of CNBr-pp65 (1×10⁷ cells/100 μg of pp65) for 1 hour. In some experiments, BSA was used as a soluble protein control, and cells were treated as for CNBr pp65 cells. All target cells were then labelled with 200 μCi of $Cr^{51}$ for 2 hours at 37° C.

Metabolic blockade with Actinomycin D (Act D) was used to prepare target cells such that they were infected with CMV but not endogenously synthesizing any CMV gene products, as previously described (11). Briefly, $Cr^{51}$ labelled fibroblast monolayers were preincubated in medium containing 20 μg/ml Act D for 30 minutes, infected with CMV (MOI of 5) in the continued presence of Act D for 4 hours, and maintained in Act D containing media during two washes and the 4 hour chromium release assay. In these experiments, control fibroblasts were infected with CMV for 4 hours in the absence of Act D.

For experiments examining the kinetics of pp65 presentation to CTL, fibroblasts were infected with CMV at an MOI=5 for 2, 4, 12, 24, 36, 48 or 66 hours and labelled with $Cr^{51}$ for 2 hours prior to use as target cells.

To prepare targets for plating, the $Cr^{51}$ labelled fibroblasts were washed three times in cold HBSS and resuspended in RPMI 10% FCS for counting. For all assays, target cells were plated in triplicates in 96 well round bottom plates at 1×10⁴ cells/well, and effector cells were added to achieve various E/T ratios in a final volume of 200 μl. Following a 4 hour incubation, plates were centrifuged at 70× g for 10 minutes and 100 μl of supernatant harvested for gamma counting. Spontaneous release was determined from target cells incubated with media alone, maximal release was determined from target cells incubated with 1% NP-40 (Sigma), and percent specific lysis was calculated using the standard formula. Spontaneous release was less than 15% for CMV-infected cells and less than 20% for CNBr-pp65 labelled cells.

Monoclonal Antibodies and Cell Surface Phenotype

Depletion of CD4 and CD8+ T cells from effector cell populations was done as previously described (11). T cell clones were phenotyped for CD3, CD4, and CD8 expression by indirect immunofluorescence using OKT3 (αCD3), OKT4 (αCD4) and OKT8 (αCD8) mAb (Ortho, Raritan, N.J.) and FITC conjugated goat antimouse Ig (Tago, Burlingame, Calif.).

Results

Recognition of pp65 by Polyclonal CD8+ CMV-specific CTL

Figure 1:
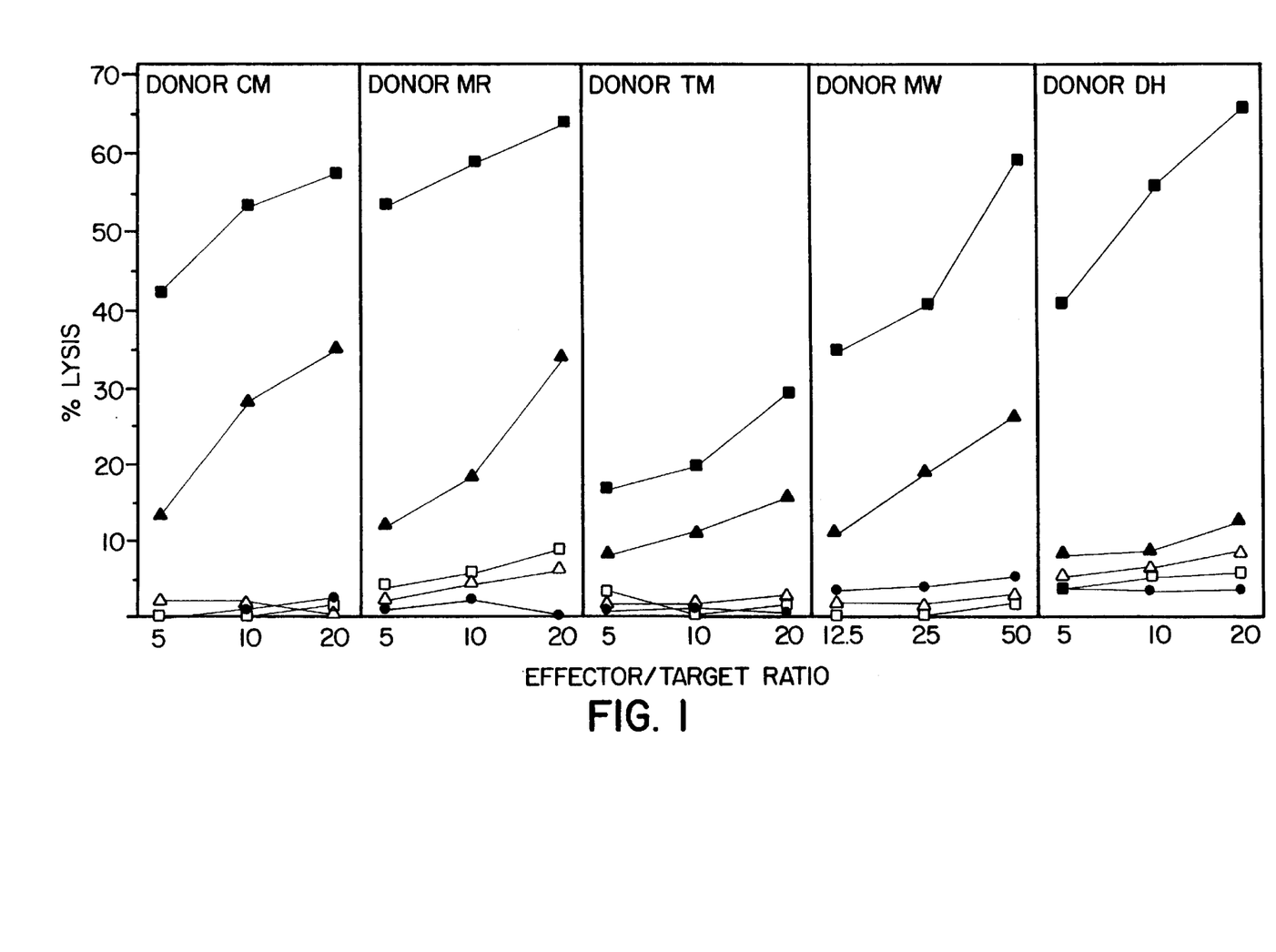
FIG. 1 demonstrates that polyclonal CMV-specific CTL lyse autologous cells from five different donors pulsed with CNBr digest of the CMV matrix protein pp65. CMV-specific CTL lines were generated from 5 CMV seropositive donors and assayed in a 4 hour chromium release assay for recognition of autologous target cells either infected for 24 hours with CMV (■), pulsed for 1 hour with CNBr cleaved pp65 (▲), or mock infected (●). Control MHC mismatched target cells were either infected for 24 hours with CMV (□), or pulsed for 1 hour with CNBr cleaved pp65 (Δ).

To determine whether pp65 would serve as a significant target antigen for a component of the CMV-specific CTL derived from CMV seropositive individuals with protective immunity, polyclonal CMV-specific CTL were activated by stimulating peripheral blood lymphocytes with autologous CMV-infected fibroblasts in short term cultures. These effector cell populations were assayed for the ability to lyse autologous and MHC mismatched fibroblasts either infected with CMV, mock-infected, or pulsed with CNBr digested pp65. Polyclonal CMV-specific CTL lines generated from four of five consecutive donors studied lysed both autologous CNBr pp65 pulsed target cells and CMV-infected cells but not mock infected targets (FIG. 1). Lysis of both CMV-infected and CNBr pp65 pulsed autologous targets was class I MHC-restricted since target cells that were mismatched for class I MHC antigens were not lysed (FIG. 1). Lysis was predominantly mediated by CD8+ T cells since selective depletion of the CD8+ T cell subset but not the CD4+subset abrogated lytic activity (Table 1).

TABLE 1

Lysis of autologous CMV-infected and CNBr pp65 pulsed fibroblasts by polyclonal CMV-specific CTL is mediated by CD8+ T cells

| Cell Line | E/T* | mAb + C | Autologous Target Cells | | | MHC Mismatched Target Cells | | |
|---|---|---|---|---|---|---|---|---|
| | | | Mock | CMV | CNBr pp65 | Mock | CMV | CNBr pp65 |
| CMαCMV | 20:1 | — | 2 | 57 | 35 | 2 | 11 | 0 |
| | | αCD4 | 1 | 58 | 38 | 0 | 6 | 0 |
| | | αCD8 | 1 | 3 | 2 | 0 | 4 | 2 |
| MRαCMV | 20:1 | — | 0 | 65 | 33 | 5 | 10 | 8 |
| | | αCD4 | 1 | 67 | 35 | 2 | 8 | 9 |
| | | αCD8 | 0 | 12 | 7 | 3 | 7 | 3 |

TABLE 1-continued

Lysis of autologous CMV-infected and CNBr pp65
pulsed fibroblasts by polyclonal CMV-specific
CTL is mediated by CD8+ T cells

| | | | Target Cell (% Lysis) | | | | | |
|---|---|---|---|---|---|---|---|---|
| Cell | | | Autologous Target Cells | | | MHC Mismatched Target Cells | | |
| Line | E/T* | mAb + C | Mock | CMV | CNBr pp65 | Mock | CMV | CNBr pp65 |
| TMαCMV | 20:1 | — | 2 | 29 | 15 | 0 | 2 | 0 |
| | | αCD4 | 1 | 33 | 14 | 0 | 3 | 0 |
| | | αCD8 | 0 | 4 | 2 | 1 | 1 | 1 |

*Effector - target ratio

Fibroblasts pulsed with native pp65 were not lysed (data not shown). These results demonstrated that in the majority of CMV seropositive individuals a component of the memory CD8+ CMV-specific CTL response activated by stimulation with autologous CMV-infected fibroblasts, recognize epitopes of the CMV matrix protein pp65. In these individuals, the lytic profile of polyclonal CTL for CNBr pp65 pulsed autologous fibroblasts suggests that pp65-specific CTL comprise a significant subset of the CMV-specific CTL response. The inability to identify CTL that recognize CNBr pp65 pulsed fibroblasts in 1 of the 5 individuals may be due to an absence of a memory CTL response specific for pp65 in this individual or to a failure of CNBr cleavage of pp65 to produce peptides similar enough to the epitopes generated by intracellular antigen processing that are recognized in the context of class I MHC by CTL of this individual.

Figure 2:
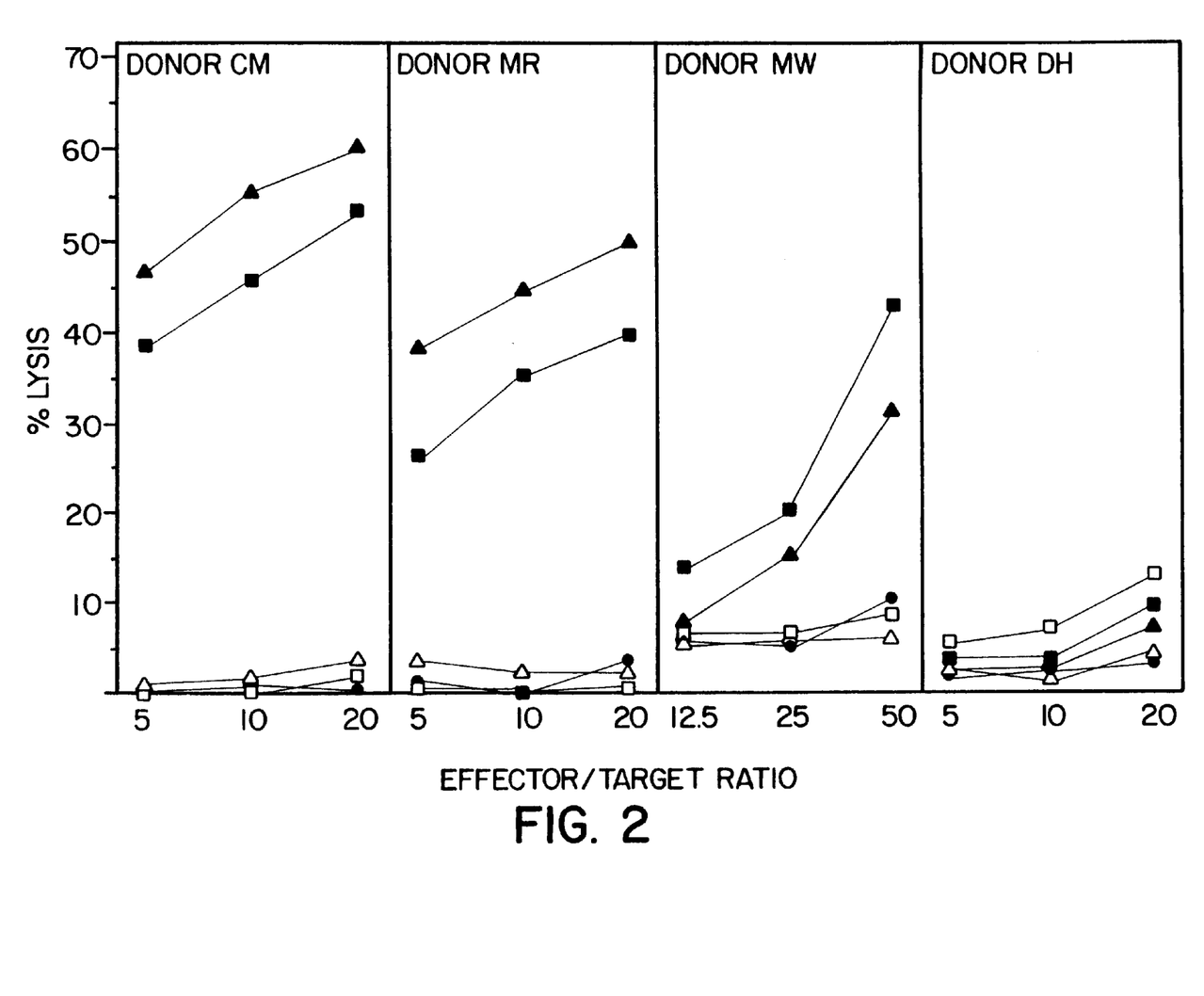
FIG. 2 demonstrates in vitro stimulation of peripheral blood lymphocytes with CNBr cleaved pp65 elicits class I MHC restricted CTL that lyse CMV infected target cells. PBL from 4 donors were stimulated with CNBr cleaved pp65 either directly (donor MW) or presented on autologous fibroblasts (donors CM, MR, and DH). Effector cells from these cultures were assayed in a 4 hour chromium release assay for lysis of autologous fibroblast target cells either infected with CMV for 24 hours (■), pulsed for 1 hour with CNBr cleaved pp65 (▲), or mocked infected (●). Control MHC mismatched target cells infected with CMV for 24 hours (□) and pulsed with CNBR cleaved pp65 (Δ) were assayed to demonstrate that lysis in class I MHC restricted.

CD8+ pp65-Specific CTL Clones Recognize CMV-Infected Cells in the Absence of Viral Gene Expression pp65 is one of the most abundant structural virion proteins (25), and thus represents an attractive candidate as a target antigen for this response. To determine if class I MHC restricted presentation of pp65 in CMV-infected cells was independent of viral gene expression, it was necessary to selectively isolate pp65-specific CTL and then determine whether those could lyse CMV infected target cells with and without viral gene blockage. The pp65 specific CTLs were isolated by culturing PBL directly with CNBr digested pp65 or by pulsing autologous γ irradiated fibroblasts with CNBr pp65 and using these cells as APC to stimulate PBL in short term cultures. In 3 of 4 donors, these stimulations consistently elicited CTL that lysed autologous CMV-infected or CNBr pp65 pulsed fibroblasts in a class I MHC-restricted fashion (FIG. 2).

CD8+ pp65-specific T cell clones were then generated from one of these lines by plating CD8+ T cells in limiting dilution cultures with γ irradiated autologous CNBr pp65 pulsed fibroblasts as both stimulators and irradiated feeder cells. From these cultures, a panel of CD3+, CD8+, CD4− T cell clones were identified that lysed autologous CMV-infected and CNBr pp65 pulsed fibroblasts but not mock infected or MHC mismatched target cells. The cytolytic reactivity of 7 representative clones is shown in Table 2.

TABLE 2

Cytolytic reactivity of seven representative
CD8+ T cell clones specific for the
CMV matrix protein pp65

| | | Target Cell (% Lysis) | | | | | |
|---|---|---|---|---|---|---|---|
| | | Autologous Cells | | | | MHC Mismatched Cells | |
| Clone | E/T* | Mock | CMV | CNBr pp65 | Mock | CMV | CNBr pp65 |
| CM1C8 | 5:1 | 0 | 30 | 57 | 0 | 0 | 0 |
| CM11D3 | 5:1 | 1 | 37 | 74 | 1 | 0 | 1 |
| CM15F11 | 5:1 | 1 | 33 | 71 | 0 | 1 | 1 |
| CM2C8 | 5:1 | 0 | 30 | 57 | 0 | 0 | 0 |
| CM16E6 | 5:1 | 1 | 31 | 70 | 1 | 2 | 1 |
| CM8A10 | 5:1 | 0 | 33 | 60 | 0 | 0 | 0 |
| CM6H12 | 5:1 | 2 | 32 | 74 | 1 | 2 | 1 |

*Effector/Target ratio.

The pp65-specific T cell clones were then assayed for the ability to lyse autologous fibroblasts infected with CMV in the presence of the RNA synthesis inhibitor ActD. The concentration of ActD used in these experiments has previously been shown to block detectable CMV gene transcription in infected cells (11). The pp65-specific T cell clones lysed autologous ActD blocked CMV-infected target cells as efficiently as target cells infected in the absence of ActD (Table 3), demonstrating that this CMV matrix protein is available for processing and presentation for CTL recognition without the requirement for viral protein synthesis following viral entry.

TABLE 3

CD8+ pp65-Specific CTL Clones Recognize
CMV-Infected Target Cells in The Absence
of Viral Gene Expression TARGET CELL (% Lysis)

| | Autologous Cells | | | | MHC Mismatched Cells | | | |
|---|---|---|---|---|---|---|---|---|
| Clone | Mock | CMV | CMV/ActD | CNBrpp65 | Mock | CMV | CMV/ActD | CNBtpp65 |
| 11D3 | 0/1/0 | 18/21/27 | 23/24/28 | 71/74/80 | 2/2/2 | 2/2/0 | 0/0/0 | 0/0/0 |
| 15C10 | 2/2/3 | 14/16/21 | 19/24/27 | 59/75/83 | 3/3/2 | 0/0/1 | 0/1/1 | 1/0/0 |
| 15F2 | 2/2/2 | 20/22/24 | 22/25/28 | 71/74/81 | 1/2/2 | 0/0/1 | 1/0/0 | 0/0/0 |
| 15F11 | 0/1/0 | 14/16/28 | 10/17/23 | 60/71/77 | 1/2/2 | 0/0/1 | 1/0/0 | 0/0/0 |
| 16E6 | 2/1/0 | 12/21/24 | 20/21/22 | 60/73/75 | 2/2/1 | 0/0/0 | 1/1/1/ | 2/0/0 |

Figure 3:
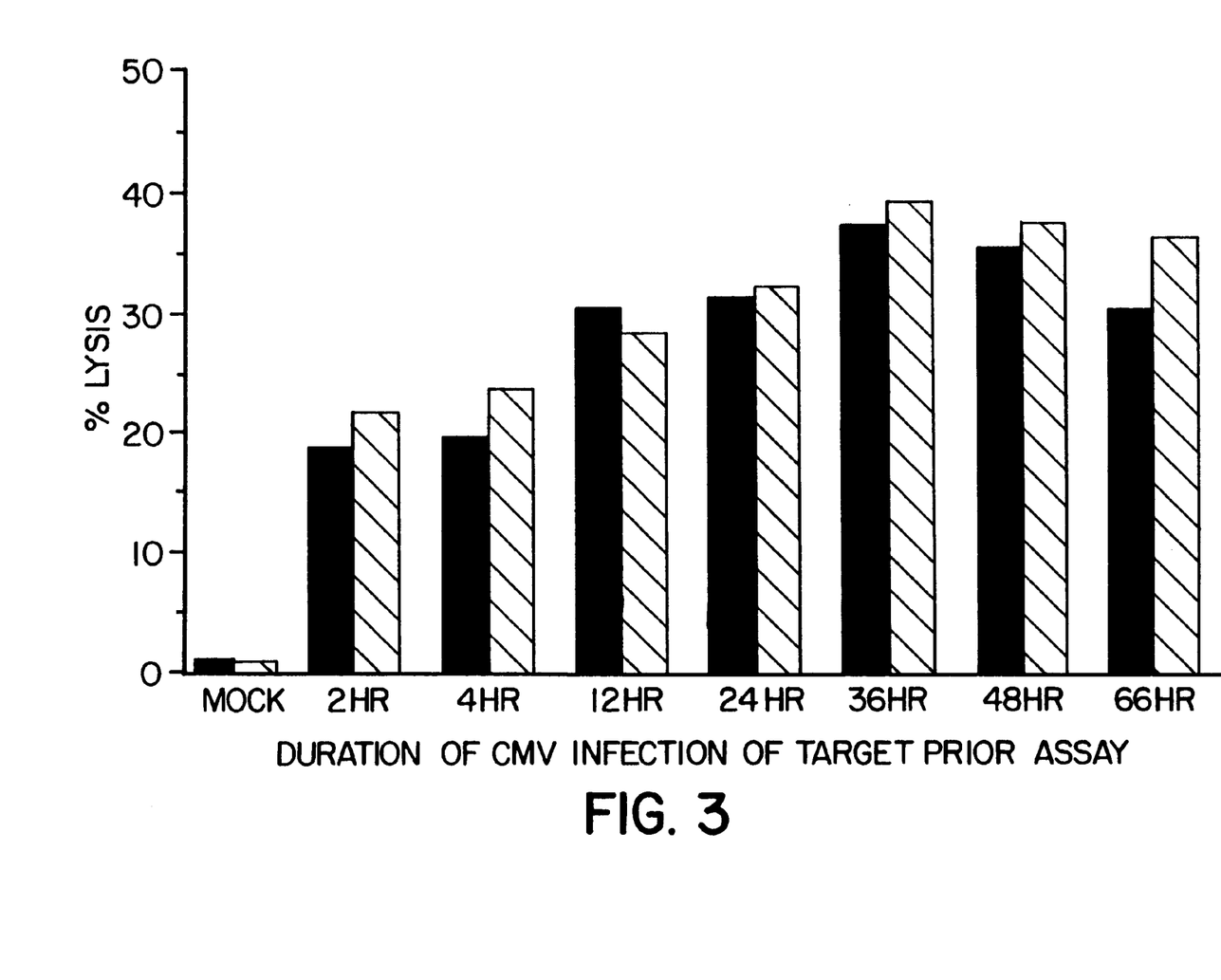
FIG. 3 demonstrates pp65-specific CTL clones lyse CMV infected cells at all stages of the viral replicative cycle. CD3+, CD8+, CTL clones were derived from the pp65-specific CTL line generated from donor CM. Clones 1C8 (■) and 2C8▨ were assayed for recognition of autologous target cells either mock infected or infected with CMV at an MOI of 5 for 2–66 hours prior to use in a 4 hour chromium release assay. The effector to target ratio in this assay was 5:1. Lysis of MHC mismatched target cells infected with CMV was <5% at all time points (data not shown).

CD8+ pp65-specific T cell clones generated from CMV seropositive donor CM (HLA A1, A2, B35, B57) as described in Table 2 were assayed for recognition of autologous and MHC mismatched fibroblast target cells either mock infected, infected with CMV for 4 hours, pretreated with ActD and infected with CMV for 4 hours or pulsed with CNBr pp65 for 1 hour. The numbers represent specific lysis of target cells at E/T ratios of 1.25:1/2.5:1/5:1.

pp65-Specific CTL Recognize CMV-Infected Cells at all Stages of the Viral Replicative Cycle To determine if pp65 is efficiently presented by CMV-infected cells throughout the replicative cycle, the recognition of autologous cells infected with CMV for various periods of time (2–66 hours) prior to use as targets in the chromium release assay was examined. These experiments demonstrated that pp65-specific T cell clones recognized target cells infected with CMV at all stages of the viral replicative cycle. Representative data is shown for two clones in FIG. 3. Lysis of CMV-infected cells by these clones is evident at the earliest time point (2 hours) after infection, and peaks at 36 and 48 hours after infection. Thus, presentation of the pp65 matrix protein in CMV infected cells for class I MHC restricted T cell recognition occurs promptly after viral entry and during all stages of the viral replicative cycle.

The structural matrix protein pp65 has been identified as a target antigen for CMV-specific class I MHC restricted CTL derived from the peripheral blood of 4 of 5 asymptomatic CMV seropositive individuals. The lytic profile observed for polyclonal CMV-specific CTL on CNBr pp65 sensitized target cells suggests that pp65 represents a significant target antigen, among others, recognized by CMV-specific CTL. The described method to identify pp65 specific CTL is based on the many observations that synthetic peptides and chemically or enzymatically cleaved protein fragments can substitute for endogenously expressed protein antigens when presented to CTL in the context of MHC on an appropriate target cell (12, 16, 17, 18, 19, 20). This approach circumvents the need to generate recombinant viral vectors expressing single CMV genes when the putative antigen can be obtained as a soluble protein. Synthetic viral peptide fragments may sensitize uninfected cells for lysis either by directly associating with class I molecules, thus bypassing the cellular processing requirement altogether, or by being internalized by the cell in an already degraded form that enables the peptide to enter the intracellular trafficking and processing pathways leading to class I MHC association and presentation (33). In either case, the result is the presence at the cell surface of class I MHC peptide complexes of sufficient density for recognition by CTL. The CNBr-pp65 digest used in the described experiments apparently works in a similar manner, except that several protein fragments are present, one or more of which would be similar to a naturally processed fragment produced in CMV-infected cells. This is consistent with observations that antigen processing events for native proteins include internalization and degradation within lysosomal compartments resulting in association with class II and not class I MHC molecules for transport to the cell surface (34). The advantage of this aspect of the invention is the simplicity and rapidity with which it can be determined whether an individual virion protein is able to serve as a CTL target antigen without the construction of recombinant vectors. The disadvantages are that not all viral proteins can be readily purified from infected cells, and chemical or enzymatic cleavage may not produce protein fragments capable of mimicking all the epitopes produced by endogenous processing in the virally infected cell.

This invention also demonstrates that CD8+ class I MHC restricted CTL specific for the matrix protein pp65, are readily isolated from the majority of healthy CMV seropositive individuals. These CTL will recognize CMV-infected cells without the requirement for viral gene expression and thus may provide an important effector cell for limiting CMV reactivation as well as for the resolution of active CMV disease.

A strong CTL response to virion proteins such as the pp65 matrix protein which are available for class I antigen processing immediately following virion entry and prior to the onset of viral replication in the infected cell is biologically attractive since such a CTL response may be particularly effective at limiting the potential for viral reactivation to progress to clinical disease. If the pp65-specific CTL response is also a major contributor to the resolution of active CMV infection, it would be expected that CMV-infected cells would be targets for CTL throughout the duration of the viral replicative cycle. Following CMV entry and uncoating, the viral genome is expressed in a cascade fashion with sequential expression of immediate early (0–2 hours), early (2–24 hours) and late (>24 hours) viral proteins (26). Abundant expression of pp65 does not occur until late stages of viral replication (27). Nevertheless, analysis of CTL induced target cell lysis after CMV infection indicated that pp65 specific lysis was present at all times post infection with a peak activity at 36–48 hours consistent with peak synthesis of this protein (25).

Studies in immunocompromised bone marrow transplant patients have identified that recovery of CD8+ CMV-specific CTL responses correlates with protection from developing CMV disease, but that greater than 50% of BMT recipients have delayed recovery of, or absent CMV-specific CTL responses for prolonged periods of time following transplant. This group of patients is at particularly high risk for developing CMV pneumonia (9). Thus, the identification of specific CTL target antigens provided by this invention is useful in the design of methods to augment CMV-specific immunity in BMT recipients. Synthetic viral peptides have recently been shown to be effective in specifically priming naive animals to generate high affinity virus-specific CTL when the peptide is conjugated to a lipoprotein or contained within a liposome (36, 37). Such an approach has the advantage of potentially eliciting CTL responses to CMV in immunosuppressed patients without the requirement for exposure to infectious virus. The demonstration that pp65 is a target antigen for CTL in the majority of seropositive individuals throughout the viral replicative cycle suggests that pp65 is an appropriate antigen to target in efforts to provide immunocompromised hosts with immunity to CMV.

Isolation and Purification pp65-CNBr Digest Peptides

This aspect of the invention includes the preparation of CNBr digests of pp65 and the isolation and purification of immunologically significant peptides from such digests.

For chemical cleavage with CNBr, pp65 was dissolved in 60% formic acid and treated overnight under argon with a 100 fold molar excess of CNBr (over methionine residues). The solvent was evaporated at room temperature under a stream of argon, the residue resuspended in water and lyophilized. The peptides were fractionated by HPLC on a Vydac C4 reverse phase column, using a 90-minute linear gradient from 100% solvent A (0.1% TFA) to 100% solvent B (TFA/$H_2O$/$CH_3CN$, 0.1/9.9/90, v/v/v/). The HPLC purified peaks from map A were subjected to amino acid sequencing (performed by City of Hope) and from map B were used for CTL analysis (performed at the Fred Hutchinson Cancer Center).

Figure 4:
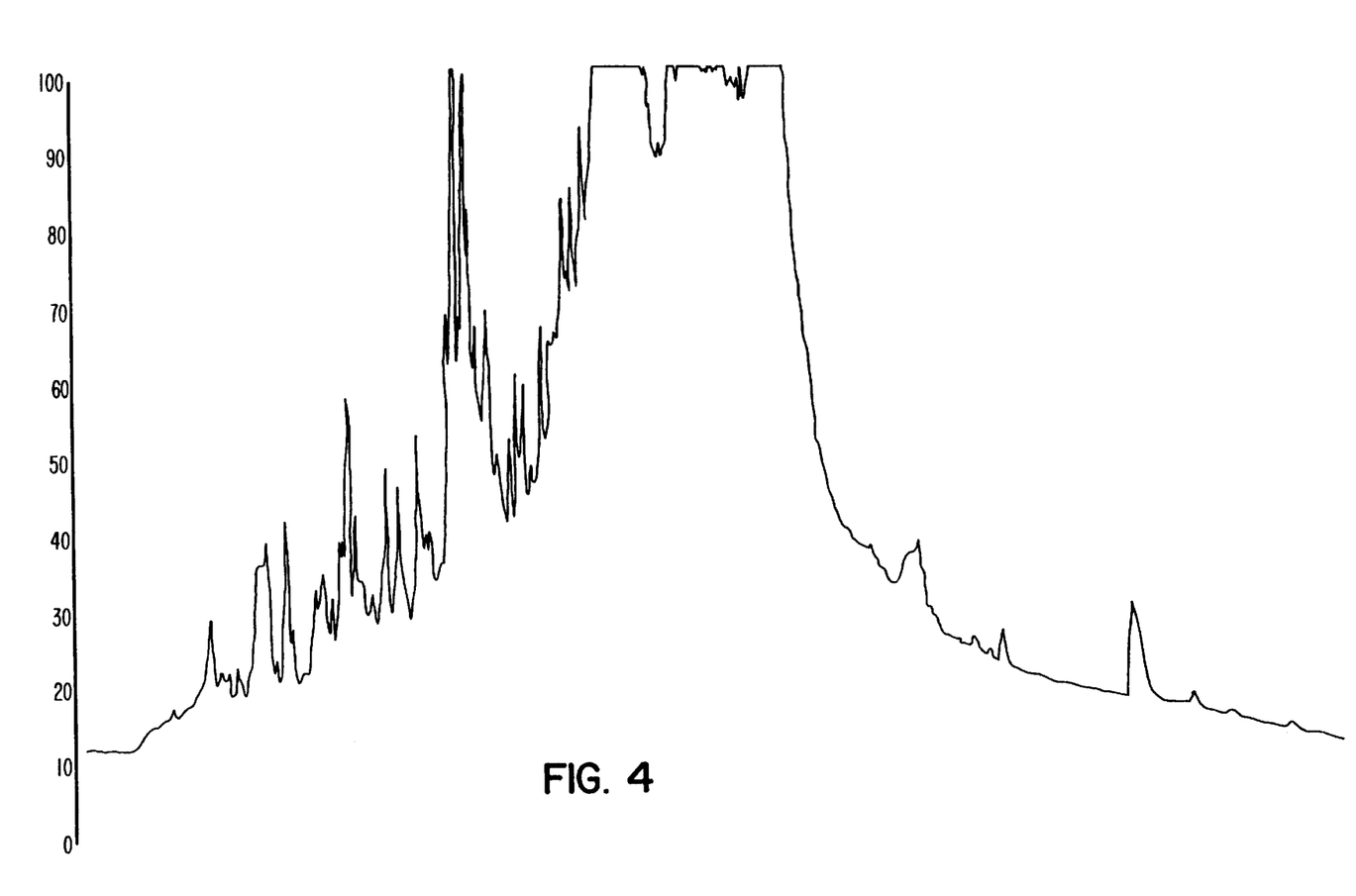
FIG. 4 is a map of a pp65-CNBr digest.

FIG. 4 is a map produced by the HPLC analysis. The HPLC purified peptide peaks designated by asterisks in FIG. 4 were sequenced. These peptides correspond to sequences 1 through 6 (Sequence ID Nos. 1–6), of this application. The invention includes the use of these six peptides or portions thereof to lyse HCMV infected cells, and as immunogens in HCMV vaccines and skin test formulations.

What is claimed is:

1. A method which comprises inducing CTLs by subjecting T cells to isolated or purified pp65 or to an isolated or purified immunologically effective fragment of pp65.

2. An isolated, purified peptide consisting of Sequence ID No. 1, or ID No. 2, or ID No. 3, or ID No. 4, or ID No. 5 or ID No. 6.

3. A man made peptide consisting of Sequence ID No. 1, or ID No. 2, or ID No. 3, or ID No. 4, or ID No. 5 or ID No. 6.

4. A method which comprises lysing HCMV infected cells by exposing said cells to isolated or purified pp65 or to an isolated or purified immunologically effective fragment of pp65.

5. A method as defined by claim 4 in which said fragment of pp65 is present in CNBr digest of pp65.

6. A method which comprises lysing HCMV infected cells by exposing said cells to isolated or purified pp65 or to an isolated or purified peptide of Sequence ID No. 1, or ID No. 2, or ID No. 3, or ID No. 4, or ID No. 5 or ID No. 6, or any combination thereof.

7. Isolated cytotoxic T lymphocytes stimulated by isolated or purified pp65 or CNBr digest of pp65 such that said lymphocytes lyse HCMV infected cells.

8. A polypeptide consisting of the peptide sequence depicted in SEQ ID NO. 1.

9. A polypeptide consisting of the peptide sequence depicted in SEQ ID NO. 2.

10. A polypeptide consisting of the peptide sequence depicted in SEQ ID NO. 3.

11. A polypeptide consisting of the peptide sequence depicted in SEQ ID NO. 4.

12. A polypeptide consisting of the peptide sequence depicted in SEQ ID NO. 5.

13. A polypeptide consisting of the peptide sequence depicted in SEQ ID NO. 6.

14. A body-treating composition which stimulates activity of human CMV-specific CTL in the peripheral blood, comprising one or more peptides with SEQ ID Nos. 1–6.

15. The composition of claim 14, which comprises a combination of two or more peptides with SEQ ID Nos. 1–6.

* * * * *

SEQUENCE LISTING

<160> NUMBER OF SEQ ID NOS: 6

<210> SEQ ID NO 1
<211> LENGTH: 98
<212> TYPE: PRT
<213> ORGANISM: HCMV

<400> SEQUENCE: 1

Ile Ser Val Leu Gly Pro Ile Ser Gly His Val Leu Lys Ala Val Phe
 1               5                  10                  15

Ser Arg Gly Asp Thr Pro Val Leu Pro His Glu Thr Arg Leu Leu Gln
                20                  25                  30

Thr Phe Ile His Val Arg Val Ser Gln Pro Ser Leu Ile Leu Val Ser
            35                  40                  45

Gln Tyr Thr Pro Asp Ser Thr Pro Cys His Arg Gly Asp Asn Gln Leu
    50                  55                  60

Gln Val Gln His Thr Tyr Phe Thr Gly Ser Glu Val Glu Asn Val Ser
65                  70                  75                  80

Val Asn Val His Asn Pro Thr Gly Arg Ser Ile Cys Pro Ser Gln Glu
                85                  90                  95

Pro Met

<210> SEQ ID NO 2
<211> LENGTH: 11
<212> TYPE: PRT
<213> ORGANISM: HCMV

<400> SEQUENCE: 2

Ser Ile Tyr Val Tyr Ala Leu Pro Leu Lys Met
 1               5                  10

<210> SEQ ID NO 3
<211> LENGTH: 33
<212> TYPE: PRT
<213> ORGANISM: HCMV

<400> SEQUENCE: 3

-continued

```
Lys Glu Pro Asp Val Tyr Tyr Thr Ser Ala Phe Val Phe Pro Thr Lys
 1               5                  10                 15
Asp Val Ala Leu Arg His Val Val Cys Ala His Glu Leu Val Cys Ser
                20                  25                 30
Met

<210> SEQ ID NO 4
<211> LENGTH: 8
<212> TYPE: PRT
<213> ORGANISM: HCMV

<400> SEQUENCE: 4

Glu Asn Thr Arg Ala Thr Lys Met
 1               5

<210> SEQ ID NO 5
<211> LENGTH: 15
<212> TYPE: PRT
<213> ORGANISM: HCMV

<400> SEQUENCE: 5

Pro Pro Trp Gln Ala Gly Ile Leu Ala Arg Asn Leu Val Pro Met
 1               5                  10                 15

<210> SEQ ID NO 6
<211> LENGTH: 62
<212> TYPE: PRT
<213> ORGANISM: HCMV

<400> SEQUENCE: 6

Val Ala Thr Val Gln Gly Gln Asn Leu Lys Tyr Gln Glu Phe Phe Trp
 1               5                  10                 15
Asp Ala Asn Asp Ile Tyr Arg Ile Phe Ala Glu Leu Glu Gly Val Trp
                20                  25                 30
Gln Pro Ala Ala Gln Pro Lys Arg Arg Arg His Arg Gln Asp Ala Leu
            35                  40                  45
Pro Gly Pro Cys Ile Ala Ser Thr Pro Lys Lys His Arg Gly
    50                  55                  60
```